United States Patent
Yang et al.

(10) Patent No.: US 10,907,182 B2
(45) Date of Patent: Feb. 2, 2021

(54) THERMOSTABLE FRUCTOSE-6-PHOSPHATE-3-EPIMERASE AND A METHOD FOR PRODUCING ALLULOSE USING THE SAME

(71) Applicant: CJ CHEILJEDANG CORPORATION, Seoul (KR)

(72) Inventors: Sungjae Yang, Suwon-si (KR); Hyun Kug Cho, Seoul (KR); Young Mi Lee, Suwon-si (KR); Seong Bo Kim, Seongnam-si (KR); Seong Jun Cho, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/314,067

(22) PCT Filed: Jun. 30, 2017

(86) PCT No.: PCT/KR2017/006985
§ 371 (c)(1),
(2) Date: Dec. 28, 2018

(87) PCT Pub. No.: WO2018/004308
PCT Pub. Date: Jan. 4, 2018

(65) Prior Publication Data
US 2019/0225997 A1 Jul. 25, 2019

(30) Foreign Application Priority Data
Jun. 30, 2016 (KR) .................. 10-2016-0082543

(51) Int. Cl.
*C12P 19/02* (2006.01)
*C12P 19/24* (2006.01)
*C12N 9/90* (2006.01)
*C12N 15/52* (2006.01)

(52) U.S. Cl.
CPC ............... *C12P 19/02* (2013.01); *C12N 9/90* (2013.01); *C12N 15/52* (2013.01); *C12P 19/24* (2013.01)

(58) Field of Classification Search
None
See application file for complete search history.

(56) References Cited

FOREIGN PATENT DOCUMENTS

| CN | 102382867 A | 3/2012 |
|---|---|---|
| KE | 10-2014-0133680 A | 11/2014 |
| KR | 10-2014-0080282 A | 6/2014 |
| KR | 10-2018-0004023 A | 1/2018 |
| WO | 2006/129954 A1 | 12/2006 |
| WO | 2015/032761 A1 | 3/2015 |
| WO | 2016/191267 A1 | 12/2016 |
| WO | 2018/004308 A2 | 1/2018 |

OTHER PUBLICATIONS

Lim et al., "Microbial metabolism and biotechnological production of $_D$-allose," Appl. Microbiol. Biotechnol. 91:229-235, 2011.
GenBank Accession No. ACM23082. 1, "Ribulose-phosphate 3-epimerase [Thermotoga neapolitana DSM 4359]," pp. 1-2, 2014.
GenBank Accession No. CP000916. 1, "Thermotoga neapolitana DSM 4359, complete genome," pp. 1-582, 2014.
Park et al., "D-Allulose Production from D-Fructose by Permeabilized Recombinant Cells of *Corynebacterium glutamicum* Cells Expressing D-Allulose 3-Epimerase *Flavonifractor plautii*," PLoS One 11(7):e0160044, pp. 1-22, 2016.
NCBI, Ribulose-phosphate 3-epimerase [Thermotoga neapolitana DSM 4359] GenBank Accession No. ACM23082.1 (Jan. 30, 2014).
Chan et al., "Structural Basis for Substrate Specificity in Phosphate Binding $(\beta/\alpha)_8$-Barrels: D-Allulose 6-Phosphate 3-Epimerase from *Escherichia coli* K-12," Biochemistry 47(36):9608-9617 (Sep. 9, 2008).
Mariano et al., "Competitive inhibitors of type B ribose 5-phosphate isomerases: design, synthesis and kinetic evaluation of new $_D$-allose and $_D$-allulose 6-phosphate derivatives," Carbohydrate Research 344:869-880 (2009).
Accession No. B9K7Z9, Version 42, 2 pages, 2016.
Accession No. B9K7Z9, Version 53, 2 pages, 2019.
Chan et al., "Structural Basis for Substrate Specificity in Phosphate Binding $(\beta/\alpha)_8$-Barrels: D-Allulose 6-Phosphate 3-Epimerase from *Escherichia coli* K-12," Biochemistry 47:9608-9617, 2008.
Extended European Search Report, dated Feb. 7, 2020, for European Application No. 17820584.5-1118/3480306, 8 pages.
Japanese Office Action, dated Feb. 1, 2010, for Japanese Application No. 2018-567065, 4 pages.

*Primary Examiner* — Suzanne M Noakes
(74) *Attorney, Agent, or Firm* — Seed IP Law Group LLP

(57) ABSTRACT

The present disclosure relates to fructose-6-phosphate-3-epimerase consisting of an amino acid sequence of SEQ ID NO: 1, a nucleic acid encoding the fructose-6-phosphate-3-epimerase, and a transformant comprising the nucleic acid. Additionally, the present disclosure relates to a composition for producing allulose, which comprises the fructose-6-phosphate-3-epimerase of the present disclosure, and a method for producing allulose using the fructose-6-phosphate-3-epimerase of the present disclosure.

10 Claims, 4 Drawing Sheets

Specification includes a Sequence Listing.

SEQUENCE LISTING

```
<160> NUMBER OF SEQ ID NOS: 8

<210> SEQ ID NO 1
<211> LENGTH: 221
<212> TYPE: PRT
<213> ORGANISM: Artificial Sequence
<220> FEATURE:
<223> OTHER INFORMATION: fructose-6-phosphate-3-epimerase

<400> SEQUENCE: 1
```

```
Met Met Val Lys Ile Ala Ala Ser Ile Leu Ala Cys Asp Leu Ala Arg
 1               5                  10                  15

Leu Ala Asp Glu Val Lys Arg Val Glu Glu His Ile Asp Met Val His
             20                  25                  30

Phe Asp Val Met Asp Gly His Phe Val Pro Asn Ile Ser Phe Gly Leu
         35                  40                  45

Pro Val Leu Lys Ala Leu Arg Lys Glu Thr Ser Leu Pro Ile Ser Val
     50                  55                  60

His Leu Met Ile Thr Asn Pro Glu Asp Tyr Val Asp Arg Phe Val Glu
 65                  70                  75                  80

Glu Gly Ala Asp Met Val Ala Val His Tyr Glu Thr Thr Pro His Leu
                 85                  90                  95

His Arg Ile Val His Arg Ile Lys Asp Leu Gly Ala Lys Ala Phe Val
            100                 105                 110

Ala Leu Asn Pro His Thr Pro Val Phe Leu Leu Ser Glu Ile Ile Thr
        115                 120                 125

Asp Val Asp Gly Val Leu Val Met Ser Val Asn Pro Gly Phe Ser Gly
    130                 135                 140

Gln Arg Phe Ile Ala Arg Ser Leu Glu Lys Ile Arg Ser Leu Lys Lys
145                 150                 155                 160

Met Ile Arg Asp Leu Gly Leu Glu Thr Glu Ile Met Val Asp Gly Gly
                165                 170                 175

Val Asn Glu Glu Asn Ala Ser Ile Leu Ile Lys Asn Gly Ala Thr Ile
            180                 185                 190

Leu Val Met Gly Tyr Gly Ile Phe Lys Asn Glu Asn Tyr Val Glu Leu
        195                 200                 205

Val Arg Ser Ile Lys Gln Glu Arg Gly Glu Ser Ala Gly
    210                 215                 220
```

<210> SEQ ID NO 2
<211> LENGTH: 666
<212> TYPE: DNA
<213> ORGANISM: Artificial Sequence
<220> FEATURE:
<223> OTHER INFORMATION: fructose-6-phosphate-3-epimerase

<400> SEQUENCE: 2

```
atgatggtaa agatcgccgc ttcaatcctt gcgtgtgatc ttgcaagact cgccgatgag    60
gtaaaaaggg tggaagaaca catagacatg gttcacttcg atgtcatgga tggacacttc   120
gttccgaaca tctcgttcgg attgccgtt ctcaaagccc tgagaaaaga accagccctt   180
cctataagtg ttcatctgat gatcacaaat ccagaggact atgtggaccg tttcgtggaa   240
gagggagcgg acatggtggc ggtccactac gagacaacgc cgcaccttca caggatagtg   300
cacaggataa aggatctcgg ggcgaaggcg ttcgtcgccc tcaacccaca cacaccggtt   360
tttctcctgt ctgagatcat aacggatgtg gatggcgtac tcgtgatgag tgtgaacccg   420
ggcttttctg gtcagagatt cattgcaagg agtctggaaa aaataaggag tctgaagaag   480
atgataaggg atctgggact cgaaacggag atcatggtcg atggtggtgt caacgaagaa   540
aacgcttcta tcttaataaa gaacggtgcg acgatcctg taatgggta cggtatcttc   600
aaaaacgaaa actatgtgga actggtgaga tccatcaagc aggaaagagg ggaatctgct   660
ggctga                                                              666
```

<210> SEQ ID NO 3
<211> LENGTH: 34

```
<212> TYPE: DNA
<213> ORGANISM: Artificial Sequence
<220> FEATURE:
<223> OTHER INFORMATION: forward primer

<400> SEQUENCE: 3
ggaacatatg atggtaaaga tcgccgcttc aatc                              34

<210> SEQ ID NO 4
<211> LENGTH: 27
<212> TYPE: DNA
<213> ORGANISM: Artificial Sequence
<220> FEATURE:
<223> OTHER INFORMATION: reverse primer

<400> SEQUENCE: 4
catactcgag cttcccctct cctatct                                      27

<210> SEQ ID NO 5
<211> LENGTH: 270
<212> TYPE: PRT
<213> ORGANISM: Artificial Sequence
<220> FEATURE:
<223> OTHER INFORMATION: polyphosphate-dependent glucokinase

<400> SEQUENCE: 5
```

Met Leu Ala Ala Ser Asp Ser Ser Gln His Gly Gly Lys Ala Val Thr
1               5                   10                  15

Leu Ser Pro Met Ser Val Ile Leu Gly Ile Asp Ile Gly Gly Ser Gly
            20                  25                  30

Ile Lys Gly Ala Pro Val Asp Thr Ala Thr Gly Lys Leu Val Ala Glu
        35                  40                  45

Arg His Arg Ile Pro Thr Pro Glu Gly Ala His Pro Asp Ala Val Lys
    50                  55                  60

Asp Val Val Glu Leu Val Arg His Phe Gly His Ala Gly Pro Val
65                  70                  75                  80

Gly Ile Thr Phe Pro Gly Ile Val Gln His Gly His Thr Leu Ser Ala
                85                  90                  95

Ala Asn Val Asp Lys Ala Trp Ile Gly Leu Asp Ala Asp Thr Leu Phe
            100                 105                 110

Thr Glu Ala Thr Gly Arg Asp Val Thr Val Ile Asn Asp Ala Asp Ala
        115                 120                 125

Ala Gly Leu Ala Glu Ala Arg Phe Gly Ala Gly Ala Gly Val Pro Gly
    130                 135                 140

Glu Val Leu Leu Leu Thr Phe Gly Thr Gly Ile Gly Ser Ala Leu Ile
145                 150                 155                 160

Tyr Asn Gly Val Leu Val Pro Asn Thr Glu Phe Gly His Leu Tyr Leu
                165                 170                 175

Lys Gly Asp Lys His Ala Glu Thr Trp Ala Ser Asp Arg Ala Arg Glu
            180                 185                 190

Gln Gly Asp Leu Asn Trp Lys Gln Trp Ala Lys Arg Val Ser Arg Tyr
        195                 200                 205

Leu Gln Tyr Leu Glu Gly Leu Phe Ser Pro Asp Leu Phe Ile Ile Gly
    210                 215                 220

Gly Gly Val Ser Lys Lys Ala Asp Lys Trp Gln Pro His Val Ala Thr
225                 230                 235                 240

Thr Arg Thr Arg Leu Val Pro Ala Ala Leu Gln Asn Glu Ala Gly Ile
                245                 250                 255

Val Gly Ala Ala Met Val Ala Ala Gln Arg Ser Gln Gly Asp
                260                 265                 270

<210> SEQ ID NO 6
<211> LENGTH: 253
<212> TYPE: PRT
<213> ORGANISM: Artificial Sequence
<220> FEATURE:
<223> OTHER INFORMATION: polyphosphate-dependent glucokinase

<400> SEQUENCE: 6

Met Gly Arg Gln Gly Met Glu Ile Leu Gly Ile Asp Ile Gly Gly Ser
1               5                   10                  15

Gly Ile Lys Gly Ala Pro Val Asp Val Glu Thr Gly Gln Leu Thr Ala
            20                  25                  30

Glu Arg Tyr Arg Leu Pro Thr Pro Glu Asn Ala Leu Pro Glu Glu Val
        35                  40                  45

Ala Leu Val Val Ala Gln Ile Val Glu His Phe Gln Trp Lys Gly Arg
    50                  55                  60

Val Gly Ala Gly Phe Pro Ala Ala Ile Lys His Gly Val Ala Gln Thr
65                  70                  75                  80

Ala Ala Asn Ile His Pro Thr Trp Ile Gly Leu His Ala Gly Asn Leu
                85                  90                  95

Phe Ser Glu Lys Cys Gly Cys Pro Val Ser Val Leu Asn Asp Ala Asp
            100                 105                 110

Ala Ala Gly Leu Ala Glu Met Ile Phe Gly Ala Gly Lys Gly Gln Lys
        115                 120                 125

Gly Val Val Leu Met Ile Thr Ile Gly Thr Gly Ile Gly Thr Ala Leu
    130                 135                 140

Phe Thr Asp Gly Ile Leu Val Pro Asn Thr Glu Leu Gly His Ile Glu
145                 150                 155                 160

Ile Arg Gly Lys Asp Ala Glu Gln Arg Ser Ser Glu Ala Ala Arg Gln
                165                 170                 175

Arg Lys Asp Trp Thr Trp Gln Gln Trp Ala Lys Arg Leu Asn Glu His
            180                 185                 190

Leu Glu Arg Leu Glu Ala Leu Phe Trp Pro Asp Leu Phe Ile Leu Gly
        195                 200                 205

Gly Gly Ala Val Lys Asn His Glu Lys Phe Phe Pro Tyr Leu Lys Leu
    210                 215                 220

Arg Thr Pro Phe Val Ala Ala Lys Leu Gly Asn Leu Ala Gly Ile Val
225                 230                 235                 240

Gly Ala Ala Trp Tyr Ala His Thr Gln Glu Thr Gln Ala
                245                 250

<210> SEQ ID NO 7
<211> LENGTH: 813
<212> TYPE: DNA
<213> ORGANISM: Artificial Sequence
<220> FEATURE:
<223> OTHER INFORMATION: polyphosphate-dependent glucokinase

<400> SEQUENCE: 7
atgctggcag ccagtgacag cagccagcat ggcgggaagg ctgttacgct atctcccatg      60
agcgtgatcc tcgggattga cataggtggg agcggcatca agggggcccc tgtggacacg     120
gcaaccggga agctggtggc cgagcgccac cgcatcccca cgcccgaggg cgcgcaccca     180
gacgcggtga aggacgtggt ggttgagctg gtgcggcatt tgggcatgc ggggccagtc      240

```
ggcatcactt tccctggcat cgtgcagcac ggccatacCC tgagcgcagc caatgtggat    300
aaagcctgga ttggcctgga cgccgacacg cttttactg aggcgaccgg tcgcgacgtg    360
accgtgatca acgacgcaga tgccgcgggg ctagcggagg cgaggttcgg ggccggggca    420
ggtgtgccgg gcgaggtgtt gctgttgacc tttgggacag gcatcggcag cgcgctgatc    480
tataacggcg tgctggtgcc caacaccgag tttgggcatc tgtatctcaa gggcgacaag    540
cacgccgaga catgggcgtc cgaccggcc cgtgagcagg gcgacctgaa ctggaagcag    600
tgggccaaac gggtcagccg gtacctccag tatctggaag gtctcttcag tcccgatctc    660
tttatcatcg gtgggggcgt gagcaagaag gccgacaagt ggcagccgca cgtcgcaaca    720
acacgtaccc gcctggtgcc cgctgccctc cagaacgagg ccggaatcgt gggggccgcg    780
atggtggcgg cgcagcggtc acaggggac taa                                 813
```

```
<210> SEQ ID NO 8
<211> LENGTH: 762
<212> TYPE: DNA
<213> ORGANISM: Artificial Sequence
<220> FEATURE:
<223> OTHER INFORMATION: polyphosphate-dependent glucokinase

<400> SEQUENCE: 8
atggggaggc agggcatgga aattttaggg attgatatcg gaggatccgg catcaaaggg     60
gctccggtgg atgtagaaac cggccagtta accgccgagc gataccgctt acccaccccc    120
gaaaatgcct tacctgaaga agtggctctg gtagttgccc aaattgtcga cactttcag    180 tggaaaggtc gtgtagggc aggatttcct gctgccatca agcacggcgt ggcacagacg    240
gccgcaaaca tccaccctac atggattgga cttcatgctg gcaaccttt cagcgaaaaa    300 tgcggatgtc ctgtctcagt gttgaatgat gcggatgctg ccggactggc ggaaatgatc    360
tttggggcag gaaaaggcca gaaagggtg gtgctgatga ttaccattgg cactggcatc    420
gggacagccc tgttcaccga tgggatattg gtccctaata ccgagttggg acatattgaa    480
attcggggca agatgccga acagcgctct tcggaagccg cccgccagcg gaaggattgg    540
acctggcaac aatgggcaaa gcgtctgaat gagcatttgg agcgcctgga agccctgttc    600
tggcccgatt tattcatcct tggtggaggg gcagtaaaaa atcatgaaaa gttcttccct    660
tatctaaaac tgcgtactcc ctttgttgca gcaaaattgg ggaatctggc tgggattgta    720
ggcgcagcgt ggtatgctca cacccaggaa acgcaagcct ga                      762
```

THERMOSTABLE FRUCTOSE-6-PHOSPHATE-3-EPIMERASE AND A METHOD FOR PRODUCING ALLULOSE USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_438USPC_SEQUENCE_LISTING.txt. The text file is 10 KB, was created on Dec. 17, 2018, and is being submitted electronically via EFS-Web.

TECHNICAL FIELD

The present disclosure relates to fructose-6-phosphate-3-epimerase and a method for producing allulose using the same.

BACKGROUND ART

D-Psicose-3-epimerase (EC 5.1.3.30) and D-tagatose-3-epimerase (EC 5.1.3.31) are known as enzymes capable of producing allulose by 3-epimerization (C3-epimerization) of D-fructose. When allulose is produced from fructose by a single enzyme reaction using the enzymes above, there is a certain level of reaction equilibrium between the fructose (i.e., the substrate) and allulose (i.e., the product) (product/substrate=about 20% to 35%). Therefore, in the case of producing high-purity allulose using the single enzyme reaction, an additional purification process for isolating and removing a high concentration of fructose from the reaction resultant is required.

On the other hand, Chan et al. (2008. Biochemistry. 47:9608-9617) reported the *Streptococcus pyogenes*-derived D-ribulose-5-phosphate-3-epimerase (EC 5.1.3.1) and the *E. coli*-derived D-allulose 6-phosphate-3-epimerase (EC 5.1.3.-) which are capable of carrying out 3-epimerization of D-fructose-6-phosphate and D-allulose-6-phosphate; however, these enzymes are not thermostable, and thus cannot be used industrially.

DISCLOSURE

Technical Problem

The present inventors have made extensive efforts to develop a method that can economically and industrially increase the rate of conversion to allulose. As a result, when allulose-6-phosphate is produced through the conversion from sucrose, starch, or maltodextrin, which are economical raw materials, to glucose or glucose-1-phosphate, glucose-6-phosphate, and fructose-6-phosphate, it was found that allulose can be produced using allulose-6-phosphate phosphatase involved in an irreversible reaction pathway. Therefore, considering that it is possible to produce allulose with one-pot enzymatic conversions, in which a plurality of enzymes involved in the allulose production pathway can be used simultaneously, and that the rate of conversion to allulose can be remarkably increased, the present inventors have completed the present disclosure by discovering a novel thermostable enzyme that can be applied to the pathway for converting the fructose-6-phosphate to allulose-6-phosphate.

Technical Solution

An object of the present disclosure is to provide fructose-6-phosphate-3-epimerase consisting of an amino acid sequence of SEQ ID NO: 1.

Another object of the present disclosure is to provide a nucleic acid encoding the fructose-6-phosphate-3-epimerase of the present disclosure.

Still another object of the present disclosure is to provide a transformant comprising the nucleic acid encoding the fructose-6-phosphate-3-epimerase of the present disclosure.

Still another object of the present disclosure is to provide a composition for producing allulose, comprising the fructose-6-phosphate-3-epimerase of the present disclosure, a microorganism expressing the same, or a culture of the microorganism.

Still another object of the present disclosure is to provide a method for producing allulose using the fructose-6-phosphate-3-epimerase of the present disclosure.

Advantageous Effects

Since the thermostable fructose-6-phosphate-3-epimerase of the present disclosure is thermostable, it can be used to exploit the pathway for converting fructose-6-phosphate to allulose-6-phosphate industrially, it is possible to proceed using the pathway for synthesizing allulose due to the use of economical raw materials, and the production of allulose is possible due to dephosphorylation of allulose-6-phosphate, which is an irreversible reaction pathway; therefore, the rate of conversion to allulose can be remarkably increased.

Additionally, in the method for producing allulose using the fructose-6-phosphate-3-epimerase of the present disclosure, the isolation/purification process can be simplified or removed because the resultant of the reaction includes a high concentration of allulose due to the increase in the rate of conversion to allulose, and therefore, the production method is advantageous in that it is simple and economical.

BEST MODE

Figure 1:
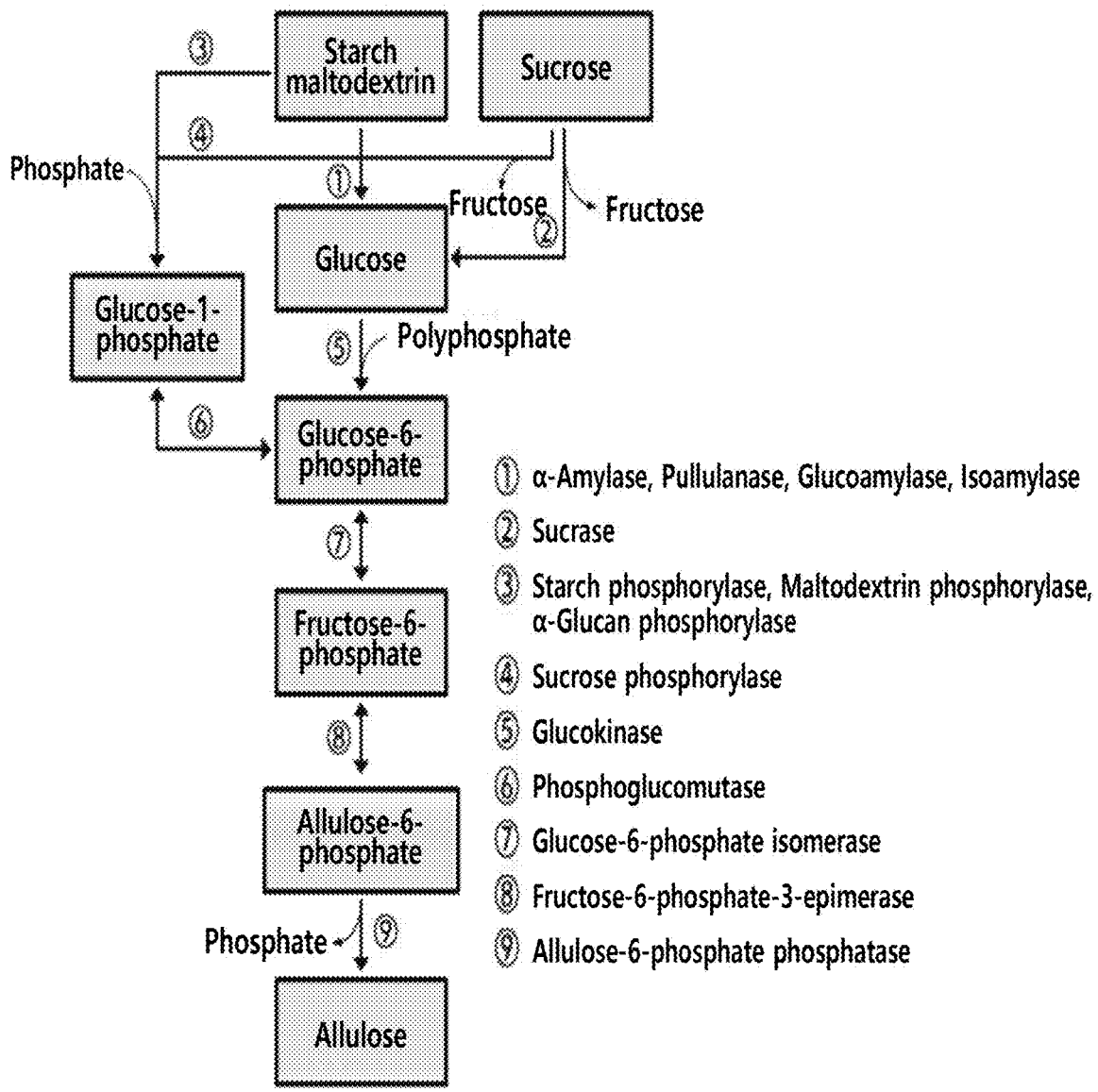
FIG. 1 shows the reaction pathway capable of producing allulose from starch (e.g., maltodextrin), sucrose, or glucose.

Hereinbelow, the present disclosure will be described in detail. Meanwhile, each of the explanations and exemplary embodiments disclosed herein can be applied to other explanations and exemplary embodiments. That is, all combinations of various factors disclosed herein belong to the scope of the present disclosure. Furthermore, the scope of the present disclosure should not be limited by the specific disclosure provided hereinbelow.

In order to achieve the object of the present disclosure, an aspect of the present disclosure provides fructose-6-phosphate-3-epimerase consisting of an amino acid sequence of SEQ ID NO: 1.

Additionally, the fructose-6-phosphate-3-epimerase of the present disclosure may comprise a polypeptide having a homology to the amino acid sequence of SEQ ID NO: 1 of at least 80%, 90%, 95%, 97%, or 99%. For example, it is apparent that a protein having an amino acid sequence having deletion, modification, substitution, or addition of some sequences falls within the scope of the present disclosure as long as it has the homology and exhibits efficacy corresponding to that of the protein consisting of the amino acid sequence of SEQ ID NO: 1.

Additionally, as long as a protein has efficacy corresponding to that of the fructose-6-phosphate-3-epimerase of the present disclosure, which consists of the amino acid sequence of SEQ ID NO: 1, it does not exclude a mutation that can occur by a meaningless sequence addition upstream or downstream of the amino acid sequence of SEQ ID NO: 1, a naturally occurring mutation, or a silent mutation. In addition, a protein including the amino acid sequence of SEQ ID NO: 1 also belongs to the scope of the present disclosure.

Further, the fructose-6-phosphate-3-epimerase may be encoded by the nucleotide sequence of SEQ ID NO: 2, or the fructose-6-phosphate-3-epimerase may be encoded by a nucleotide sequence having a homology to the nucleotide sequence of SEQ ID NO: 2 of at least 80%, 90%, 95%, 97%, or 99%, but is not limited thereto. Based on codon degeneracy, it is apparent that proteins which consist of the amino acid sequence of SEQ ID NO: 1, or polynucleotides which can be translated into proteins having a homology to the above proteins, can also be included in the scope of the present disclosure.

As used herein, the term "homology" refers to a degree of matching with a given amino acid sequence or nucleotide sequence, and the homology may be expressed as a percentage. In the present disclosure, a homology sequence having an activity which is identical or similar to the given amino acid sequence or nucleotide sequence is expressed as "% homology". The homology sequence may be determined by, for example, standard software, specifically, BLAST 2.0, which calculates the parameters such as score, identity, similarity, etc., or by comparing the sequences in a Southern hybridization experiment under defined stringent conditions, and defining appropriate hybridization conditions is within the skill of the art, and may be determined by a method well known to those skilled in the art (for example, J. Sambrook et al., Molecular Cloning, A Laboratory Manual, 2nd Edition, Cold Spring Harbor Laboratory press, Cold Spring Harbor, N.Y., 1989; F. M. Ausubel et al., Current Protocols in Molecular Biology, John Wiley & Sons, Inc., New York). As used herein, the term "stringent conditions" refers to conditions that are designed to permit specific hybridization between polynucleotides. For example, these conditions are specifically described in the literature (e.g., J. Sambrook et al., supra).

In the present disclosure, the stringent conditions may be adjusted to determine the homology. In order to confirm the homology between polynucleotides, hybridization conditions of low stringency, corresponding to a $T_m$ value of 55° C., may be used. For example, conditions of 5×SSC, 0.1% SDS, 0.25% milk, and no formamide; or 30% formamide, 5×SSC, and 0.5% SDS may be used. Hybridization conditions of mild stringency correspond to high $T_m$ values; for example, 40% formamide and 5× or 6×SSC may be used. Hybridization conditions of high stringency correspond to the highest $T_m$ values; for example, 50% formamide and 5× or 6×SSC may be used, but the hybridization conditions are not limited to the examples above.

Hybridization requires that two nucleic acids have complementary sequences, although mismatches between bases are possible depending on the stringency of hybridization. The term "complementary" is used to describe the relationship between nucleotide bases that are capable of being hybridized with each other. For example, with respect to DNA, adenosine is complementary to thymine and cytosine is complementary to guanine. Therefore, the present disclosure may also include substantially similar nucleic acid sequences as well as isolated nucleic acid fragments complementary to the entire sequence.

Specifically, the polynucleotide having homology can be detected using hybridization conditions including a hybridization step at a $T_m$ value of 55° C. and using the above-described conditions. In addition, the $T_m$ value may be 60° C., 63° C., or 65° C., but is not limited thereto. Those skilled in the art can appropriately adjust the $T_m$ value according to its purpose.

The appropriate stringency of hybridizing the polynucleotides is dependent on the length and degree of complementarity of the polynucleotides, and the variables are well known in the art. As the similarity or homology between the two nucleotides becomes greater, the $T_m$ value for hybrids of the polynucleotides having such sequence becomes greater. The relative stability for the hybridization of the polynucleotides (corresponding to a higher $T_m$ value) decreases in the following order: RNA:RNA, DNA:RNA, DNA:DNA. The calculation formula of the $T_m$. values for hybrids, the length of which is greater than 100 nucleotides, is published in the art (Sambrook et al., supra, 9.50-9.51). For hybridization with shorter polynucleotides, e.g., oligonucleotides, the mismatch position may be more important, and the length of the oligonucleotides may determine the specificity thereof (Sambrook et al., supra, 11.7-11.8).

Specifically, the polynucleotides may be detected using the following hybridization conditions: 1) a hybridization step with a salt concentration lower than 500 mM and a temperature of at least 37° C.; and a washing step at at least 63° C. with 2×SSPE; 2) a hybridization step with a salt concentration lower than 200 mM and a temperature of at least 37° C.; or 3) both hybridization and washing steps at 63° C. with 2×SSPE.

The length of the hybridization nucleic acid can be, for example, at least about 10 nucleotides, 15 nucleotides, 20 nucleotides, or at least 30 nucleotides. In addition, those skilled in the art can adjust the temperature and the washing solution salt concentration as needed depending on factors such as the length of the probe.

The fructose-6-phosphate-3-epimerase of the present disclosure may be an enzyme derived from *Thermotoga* sp., and specifically may be an enzyme derived from *Thermotoga neapolitana*, but is not limited thereto.

Another aspect of the present disclosure provides a nucleic acid encoding the fructose-6-phosphate-3-epimerase of the present disclosure.

Still another aspect of the present disclosure provides a transformant comprising the nucleic acid encoding the fructose-6-phosphate-3-epimerase of the present disclosure.

As used herein, the term "transformation" refers to a process of introducing into a host cell a vector including a nucleic acid encoding a target protein, thereby enabling the expression of the protein encoded by the nucleic acid in the host cell. For the transformed nucleic acid, it does not matter whether the transformed nucleic acid is inserted into the chromosome of a host cell and located therein or located outside the chromosome, as long as it can be expressed in the host cell, and both cases are included. Additionally, the nucleic acid includes DNA and RNA which encode the target protein. The nucleic acid may be inserted in any form as long as it can be introduced into a host cell and expressed therein. For example, the nucleic acid may be introduced into a host cell in the form of an expression cassette, which is a gene construct including all essential elements required for self-expression. The expression cassette may conventionally include a promoter operably linked to the nucleic acid, a transcription termination signal, a ribosome-binding domain, and a translation termination signal. The expression cassette may be in the form of an expression vector capable of self-replication. Additionally, the nucleic acid may be introduced into a host cell as it is and operably linked to a sequence essential for its expression in the host cell, but the nucleic acid is not limited thereto.

Additionally, as used herein, the term "operably linked" refers to a functional linkage between a promoter sequence, which initiates and mediates the transcription of the nucleic acid encoding the target protein of the present disclosure, and the above gene sequence.

The method of the present disclosure for transforming the vector includes any method of introducing a nucleic acid into a cell, and may be carried out by selecting a suitable standard technique known in the art according to a host cell. Examples of the method may include electroporation, calcium phosphate ($CaPO_4$) precipitation, calcium chloride ($CaCl_2$) precipitation, microinjection, a polyethyleneglycol (PEG) technique, a DEAE-dextran technique, a cationic liposome technique, a lithium acetate-DMSO technique, etc., but are not limited thereto.

As the host cell, it is preferable to use a host having a high efficiency of introducing DNA and a high efficiency of expressing the introduced DNA. For example, it may be *E. coli*, but is not limited thereto.

Still another aspect of the present disclosure provides a composition for producing allulose, comprising the fructose-6-phosphate-3-epimerase of the present disclosure, a microorganism expressing the fructose-6-phosphate-3-epimerase of the present disclosure, or a culture of the microorganism expressing the fructose-6-phosphate-3-epimerase of the present disclosure.

The composition of the present disclosure for producing allulose may further comprise an enzyme involved in the allulose-producing pathway (see FIG. 1) of the present disclosure, a microorganism expressing the enzyme involved in the allulose-producing pathway of the present disclosure, or a culture of the microorganism expressing the enzyme involved in the allulose-producing pathway of the present disclosure. However, this is merely an example; that is, an enzyme to be contained in the composition of the present disclosure for producing allulose and a substrate used for the production of allulose are not limited, as long as allulose can be produced by using the fructose-6-phosphate-3-epimerase of the present disclosure.

The composition of the present disclosure for producing allulose may further comprise allulose-6-phosphate phosphatase, a microorganism expressing the allulose-6-phosphate phosphatase, or a culture of the microorganism expressing the allulose-6-phosphate phosphatase.

Additionally, the composition of the present disclosure for producing allulose may further comprise: (a) (i) starch, maltodextrin, sucrose, or a combination thereof, glucose, glucose-1-phosphate, glucose-6-phosphate, or fructose-6-phosphate; (ii) phosphate; (iii) allulose-6-phosphate phosphatase; (iv) glucose-6-phosphate isomerase; (v) phosphoglucomutase or glucokinase; and/or (vi) α-glucanophosphorylase, starch phosphorylase, maltodextrin phosphorylase, sucrose phosphorylase, α-amylase, pullulanase, isoamylase, glucoamylase, or sucrase; or (b) a microorganism expressing any of the enzymes or a culture of the microorganism expressing any of the enzymes, but is not limited thereto.

Specifically, the starch/maltodextrin phosphorylase (EC 2.4.1.1) and α-glucanophosphorylase of the present disclosure may include any proteins as long as these are proteins that are subjected to phosphoryl transfer from phosphate to glucose, thereby having the activity of producing glucose-1-phosphate from starch or maltodextrin. The sucrose phosphorylase (EC 2.4.1.7) of the present disclosure may include any protein as long as it is a protein that is subjected to phosphoryl transfer from phosphate to glucose, thereby having the activity of producing glucose-1-phosphate from sucrose. The α-amylase (EC 3.2.1.1), pullulanase (EC 3.2.1.41), glucoamylase (EC 3.2.1.3), and isoamylase of the present disclosure, which are enzymes for starch saccharification, may include any proteins as long as these are proteins having the activity of converting starch or maltodextrin to glucose. The sucrase (EC 3.2.1.26) of the present disclosure may include any protein as long as it is a protein having the activity of converting sucrose to glucose. The phosphoglucomutase (EC 5.4.2.2) of the present disclosure may include any protein as long as it is a protein having the activity of converting glucose-1-phosphate to glucose-6-phosphate. The glucokinase may include any protein as long as it is a protein capable of transferring phosphate to glucose, thereby having the activity of converting to glucose-6-phosphate. Specifically, the glucokinase may be a polyphosphate-dependent glucokinase, and more specifically may be a polyphosphate-dependent glucokinase derived from *Deinococcus geothermalis* consisting of the amino acid sequence of SEQ ID NO: 5 and the nucleotide sequence of SEQ ID NO: 7, or may be a polyphosphate-dependent glucokinase derived from *Anaerolinea thermophila* consisting of the amino acid sequence of SEQ ID NO: 6 and the nucleotide sequence of SEQ ID NO: 8. The glucose-6-phosphate isomerase of the present disclosure may include any protein as long as it is a protein having an activity of converting glucose-6-phosphate to fructose-6-phosphate. The allulose-6-phosphate phosphatase of the present disclosure may include any protein as long as it is a protein having an activity of converting allulose-6-phosphate to allulose. More specifically, the allulose-6-phosphate phosphatase may be a protein having an activity of irreversibly converting allulose-6-phosphate to allulose.

Still another aspect of the present disclosure provides a method for producing allulose, comprising: converting fructose-6-phosphate to allulose-6-phosphate by reacting the fructose-6-phosphate with fructose-6-phosphate-3-epimerase consisting of an amino acid sequence of SEQ ID NO: 1, a microorganism expressing the fructose-6-phosphate-3-epimerase, or a culture of the microorganism expressing the fructose-6-phosphate-3-epimerase.

The production method of the present disclosure may further comprise converting allulose-6-phosphate to allulose by reacting the allulose-6-phosphate with allulose-6-phosphate phosphatase, a microorganism expressing the allulose- 6-phosphate phosphatase, or a culture of the microorganism expressing the allulose-6-phosphate phosphatase, after converting the fructose-6-phosphate of the present disclosure to the allulose-6-phosphate.

Additionally, the production method of the present disclosure may further comprise converting glucose-6-phosphate to fructose-6-phosphate by reacting the glucose-6-phosphate with glucose-6-phosphate isomerase, a microorganism expressing the glucose-6-phosphate isomerase, or a culture of the microorganism expressing the glucose-6-phosphate isomerase, prior to converting the fructose-6-phosphate of the present disclosure to allulose-6-phosphate.

Additionally, the production method of the present disclosure may further comprise converting glucose-1-phosphate to glucose-6-phosphate by reacting the glucose-1-phosphate with phosphoglucomutase, a microorganism expressing the phosphoglucomutase, or a culture of the microorganism expressing the phosphoglucomutase, prior to converting the glucose-6-phosphate of the present disclosure to fructose-6-phosphate.

Additionally, the production method of the present disclosure may further comprise converting glucose to glucose-6-phosphate by reacting the glucose with glucokinase, a microorganism expressing the glucokinase, or a culture of the microorganism expressing the glucokinase, and phosphate, prior to converting the glucose-6-phosphate of the present disclosure to fructose-6-phosphate.

Additionally, the production method of the present disclosure may further comprise converting starch, maltodextrin, sucrose, or a combination thereof to glucose-1-phosphate by reacting the starch, maltodextrin, sucrose, or combination thereof with phosphate and α-glucanophosphorylase, starch phosphorylase, maltodextrin phosphorylase, or sucrose phosphorylase; a microorganism expressing the phosphorylase; or a culture of the microorganism expressing the phosphorylase, prior to converting the glucose-1-phosphate of the present disclosure to glucose-6-phosphate.

Additionally, the production method of the present disclosure may further comprise converting starch, maltodextrin, sucrose, or a combination thereof to glucose by reacting the starch, maltodextrin, sucrose, or combination thereof with α-amylase, pullulanase, glucoamylase, sucrase, or isoamylase; a microorganism expressing the amylase, pullulanase, or sucrase; or a culture of the microorganism expressing the amylase, pullulanase, or sucrase, prior to converting the glucose of the present disclosure to glucose-6-phosphate.

The production method of the present disclosure may further comprise converting glucose to starch, maltodextrin, or sucrose by reacting the glucose with 4-α-glucanotransferase, a microorganism expressing the 4-α-glucanotransferase, or a culture of the microorganism expressing the 4-α-glucanotransferase.

In the production method of the present disclosure, the "reaction" may be carried out at a pH of 5.0 to 10.0, a temperature of 50° C. to 90° C., and/or for 1 minute to 24 hours. Specifically, the reaction of the present disclosure may be carried out at a pH of 5.0 to 9.0, a pH of 5.0 to 8.0, a pH of 5.0 to 7.0, a pH of 5.0 to 6.0, a pH of 6.0 to 10.0, a pH of 6.0 to 9.0, a pH of 6.0 to 8.0, a pH of 6.0 to 7.0, a pH of 7.0 to 10.0, a pH of 7.0 to 9.0, a pH of 7.0 to 8.0, a pH of 8.0 to 10.0, a pH of 8.0 to 9.0, or a pH of 9.0 to 10.0. Additionally, the reaction of the present disclosure may be carried out at 55° C. to 90° C., 60° C. to 90° C., 60° C. to 75° C., 65° C. to 75° C., or 60° C. to 70° C. Additionally, the reaction of the present disclosure may be carried out for 1 minute to 12 hours, 1 minute to 6 hours, 1 minute to 3 hours, 1 minute to 1 hour, 5 minutes to 24 hours, 5 minutes to 12 hours, 5 minutes to 6 hours, 5 minutes to 3 hours, 5 minutes to 1 hour, 10 minutes to 24 hours, 10 minutes to 12 hours, 10 minutes to 6 hours, 10 minutes to 3 hours, or 10 minutes to 1 hour.

Still another aspect of the present disclosure provides a method for producing allulose, comprising reacting starch, maltodextrin, sucrose, or a combination thereof, and phosphate with (a) allulose-6-phosphate phosphatase; fructose-6-phosphate-3-epimerase consisting of an amino acid sequence of SEQ ID NO: 1; glucose-6-phosphate isomerase; phosphoglucomutase or glucokinase; and α-glucanophosphorylase, starch phosphorylase, maltodextrin phosphorylase, sucrose phosphorylase, α-amylase, pullulanase, isoamylase, glucoamylase, or sucrase; or (b) a microorganism expressing any of the enzymes or a culture of the microorganism.

MODE FOR INVENTION

Hereinbelow, the present disclosure will be described in detail with accompanying exemplary embodiments. However, the exemplary embodiments disclosed herein are only for illustrative purposes and should not be construed as limiting the scope of the present disclosure.

Example 1: Preparation of Recombinant Expression Vector Containing Gene of fructose-6-phosphate-3-epimerase, and Transformed Microorganism In order to discover novel thermostable fructose-6-phosphate-3-epimerase, a gene was isolated from *Thermotoga neapolitana*, a thermophilic microorganism, and then a recombinant expression vector and a transformed microorganism were produced.

Specifically, based on gene sequences of *Thermotoga neapolitana* registered in Genbank, fp3e, which is a gene expected to encode fructose-6-phosphate-3-epimerase, was selected. Thereafter, based on the information of its amino acid sequence (SEQ ID NO: 1) and nucleotide sequence (SEQ ID NO: 2), a forward primer (SEQ ID NO: 3) and a reverse primer (SEQ ID NO: 4) were devised and synthesized. Polymerase chain reaction (PCR) was carried out with the synthesized primers using *Thermotoga neapolitana* chromosomal DNA (genomic DNA) as a template. Specifically, PCR was carried out for a total of 25 cycles under the following conditions: denaturation at 95° C. for 30 seconds, annealing at 55° C. for 30 seconds, and polymerization at 68° C. for 2 minutes. The resultants were inserted into pET21a (Novagen Inc.), which is a plasmid vector for expression in *E. coli*, using restriction enzymes Nde and Xho, and then a recombinant expression vector was constructed and named as CJ_tn_fp3e. CJ_tn_fp3e was transformed into the *E. coli* strain BL21(DE3) by a conventional transformation method (Sambrook et al. 1989) to prepare a microorganism transformed to a recombinant vector including the nucleotide sequence of SEQ ID NO: 2, and this was designated as *E. coli* BL21(DE3)/CJ_tn_fp3e.

The strain *E. coli* BL21(DE3)/CJ_tn_fp3e was deposited to the Korean Culture Center of Microorganisms (KCCM), which is an international depositary authority under the Budapest Treaty, on Jun. 23, 2016, and assigned Accession No. KCCM11848P.

Example 2: Preparation of Recombinant Enzyme

In order to prepare a recombinant enzyme (hereinafter referred to as FP3E), *E. coli* BL21(DE3)/CJ_tn_fp3e was inoculated into a culture tube containing 5 mL of LB liquid medium, and then a seed culture was initiated in a shaking incubator at 37° C. until the absorbance at 600 nm reached 2.0. The seed culture solution was inoculated into a culture flask containing the LB liquid medium, and the main culture was carried out. When the absorbance at 600 nm reached 2.0, 1 mM IPTG was added to induce expression/production of FP3E. The seed culture and main culture were carried out at a stirring rate of 200 rpm at a temperature of 37° C. Upon completion of the main culture, the culture solution was centrifuged at 4° C. at 8,000×g for 20 minutes, and then cells were recovered. The recovered cells were washed twice with a 50 mM Tris-HCl buffer (pH 7.0), suspended in the same buffer, and then the cells were disrupted using an ultrasonic cell disruptor. The cell debris was centrifuged at 4° C. at 13,000×g for 20 minutes, and then only the supernatant was obtained. FP3E was purified from the supernatant using His-tag affinity chromatography. The purified recombinant enzyme solution was dialyzed with a 50 mM Tris-HCl buffer (pH 7.0), and then the resultants were used for property analysis of the enzyme.

Figure 2:
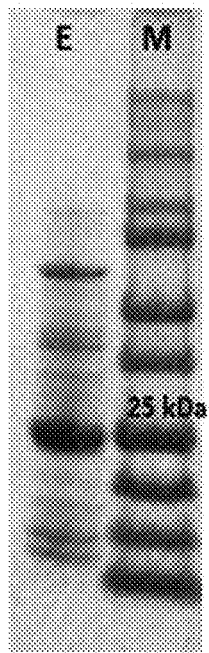
FIG. 2 shows the results of analysis of the molecular weight of the fructose-6-phosphate-3-epimerase (E: FP3E) of the present disclosure by protein electrophoresis (SDS-PAGE). "M" represents a protein size marker.

The molecular weight was confirmed by SDS-PAGE analysis, and as a result, it was found that the molecular weight of the purified FP3E was about 25 kDa (indicated as "E" in FIG. 2).

Example 3: Confirmation of Activity of FP3E

In order to analyze the conversion activity of FP3E from fructose-6-phosphate to allulose-6-phosphate, fructose-6-phosphate (50 mM) was suspended in a 50 mM Tris-HCl buffer (pH 7.0), and the purified FP3E (0.1 unit/mL) was added thereto. Thereafter, the resultants were reacted at 70° C. for 1 hour.

Due to the absence of the reference material of allulose-6-phosphate at present, it is impossible to determine whether allulose-6-phosphate is produced. Therefore, after converting allulose-6-phosphate to allulose using a phytase, which is allulose-6-phosphate phosphatase, the conversion activity was measured according to the production of allulose. Specifically, upon completion of the reaction, a phytase (10 unit/mL) was added and then reacted at 37° C. for 1 hour to dephosphorylate both the substrate, e.g., fructose-6-phosphate, and the product, e.g., allulose-6-phosphate. Thereafter, the fructose and allulose were analyzed by HPLC. HPLC analysis was carried out using an Aminex HPX-87C column (Bio-rad Inc.) while flowing the reaction product in the mobile phase at a flow rate of 0.5 mL/min at 80° C. The fructose and allulose were detected by a Refractive Index Detector.

Figure 3:
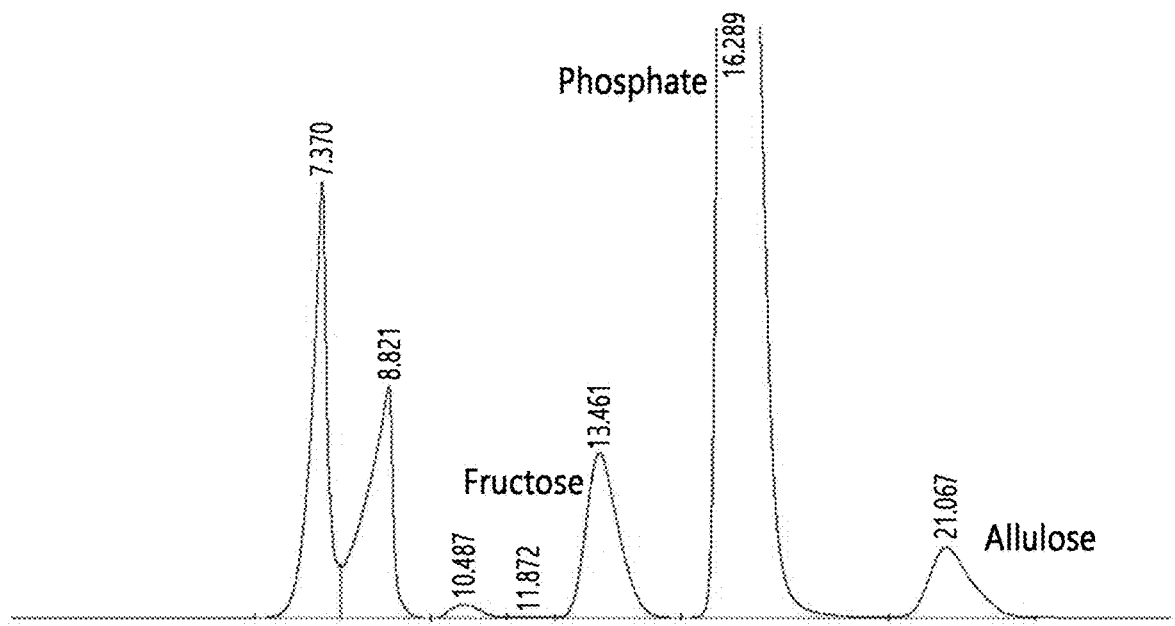
FIG. 3 is a graph showing the conversion activity of the fructose-6-phosphate-3-epimerase of the present disclosure from fructose-6-phosphate to allulose-6-phosphate.

As a result, the fructose and allulose were detected in the reaction product of FP3E (FIG. 3), and thus it was confirmed that FP3E had the activity of producing allulose-6-phosphate by 3-epimerization of fructose-6-phosphate (FIG. 3).

Example 4: Confirmation of Activity of FP3E According to pH, Temperature, and Addition of Metal Ion 4-1. Conformation of Activity According to pH In order to investigate the influence of pH on FP3E, the purified FP3E (0.1 unit/mL) was added to fructose-6-phosphate (50 mM) suspended in a 50 mM buffer with various pHs (pH 4.0 to 7.0, sodium citrate; pH 6.0 to 8.0, potassium phosphate: pH 7.0 to 9.0, Tris-HCl), and then reacted at 70° C. for 10 minutes. Thereafter, the resultants were reacted with a phytase under the same conditions as in Example 3, and the allulose was quantitatively analyzed by HPLC.

Figure 4:
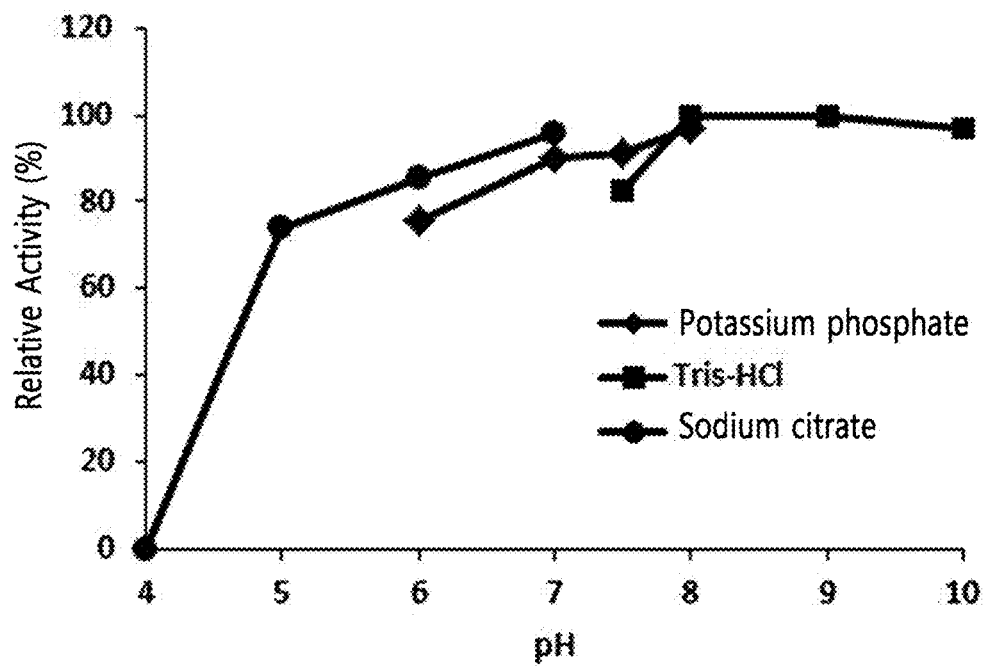
FIG. 4 is a graph showing the activity of the fructose-6-phosphate-3-epimerase of the present disclosure according to the buffer solution and pH range.
Figure 5:
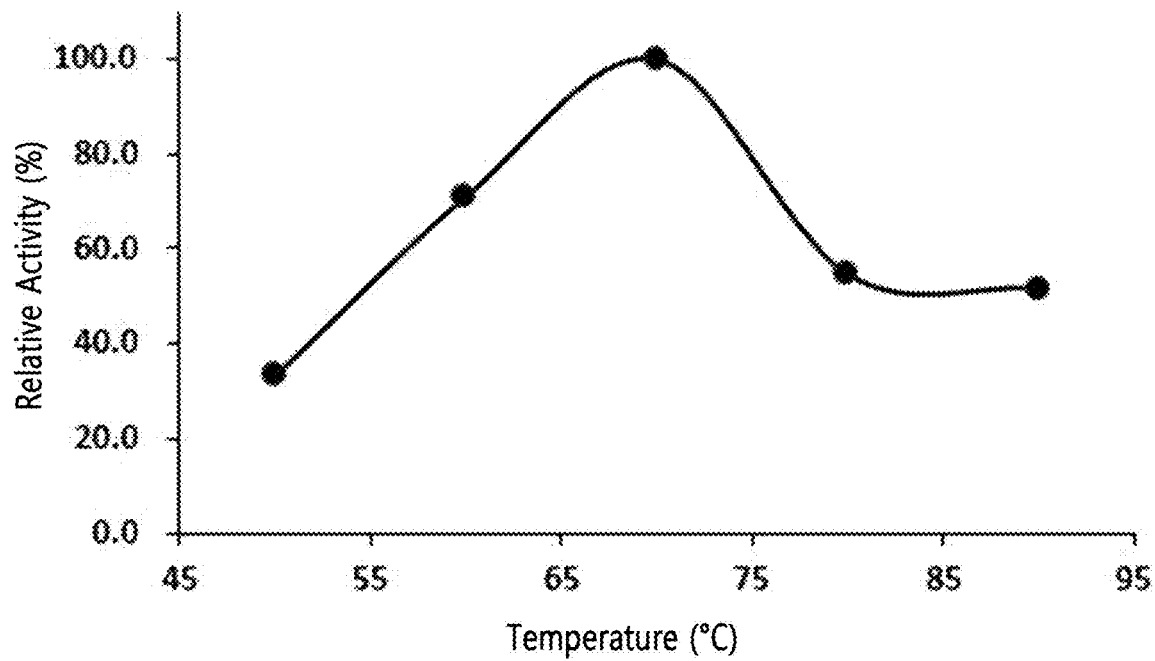
FIG. 5 is a graph showing the activity of the fructose-6-phosphate-3-epimerase of the present disclosure according to temperature.

As a result, it was confirmed that FP3E showed the maximum activity at a pH of 7.0 to 8.0, and that FP3E maintained 70% or higher of its activity at a very broad pH range (5.0 to 10.0) compared to the maximum activity (FIG. 4).

4-2. Confirmation of Activity According to Addition of Metal Ion

In order to investigate the effect of addition of a metal ion on the activity of FP3E, each of the metal ions (e.g., $NiSO_4$, $CuSO_4$, $MnSO_4$, $CaCl_2$, $ZnSO_4$, $MgSO_4$, $MgCl_2$, $FeSO_4$, NaCl, LiCl, and KCl) was added to fructose-6-phosphate (50 mM) suspended in a 50 mM Tris-HCl buffer (pH 7.0) to a final concentration of 0.5 mM. For the removal of the metal ions, FP3E (0.1 unit/mL), which was dialyzed by treating with 10 mM EDTA, was added thereto, and then the resultants were reacted at 70° C. for 10 minutes. Thereafter, the resultants were reacted with a phytase under the same conditions as in Example 3, and the allulose was quantitatively analyzed by HPLC.

Figure 6:
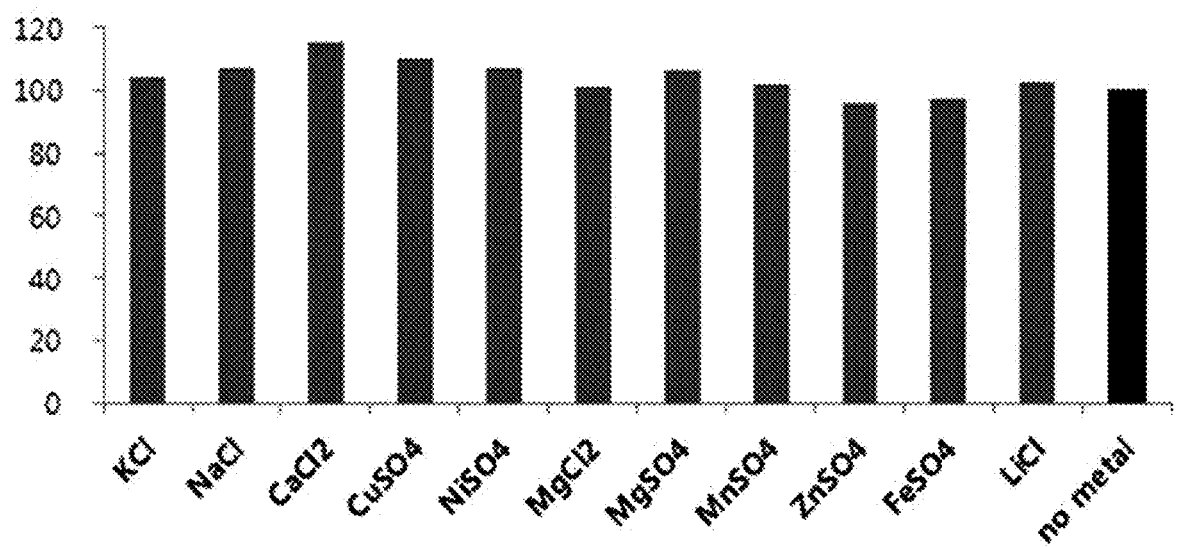
FIG. 6 is a graph showing the activity of the fructose-6-phosphate-3-epimerase of the present disclosure upon addition of a metal ion.

As a result, the activity of FP3E was slightly increased when Ca and Cu ions were added, but there was almost no change in the enzyme activity when other metal ions were added. Therefore, it was confirmed that FP3E was not a metalloenzyme (FIG. 6).

While the present disclosure has been described with reference to the particular illustrative embodiments, it will be understood by those skilled in the art to which the present disclosure pertains that the present disclosure may be embodied in other specific forms without departing from the technical spirit or essential characteristics of the present disclosure. Therefore, the embodiments described above are considered to be illustrative in all respects and not restrictive. Furthermore, the scope of the present disclosure is defined by the appended claims rather than the detailed description, and it should be understood that all modifications or variations derived from the meanings and scope of the present disclosure and equivalents thereof are included in the scope of the appended claims.

The invention claimed is:

1. A method for producing allulose, comprising:
   converting fructose-6-phosphate to allulose-6-phosphate by reacting said fructose-6-phosphate with a fructose-6-phosphate-3-epimerase consisting of the amino acid sequence of SEQ ID NO: 1, a microorganism expressing said fructose-6-phosphate-3-epimerase, or a culture of said microorganism comprising said fructose-6-phosphate-3-epimerase, and
   converting allulose-6-phosphate to allulose.

2. The method according to claim 1, wherein the converting allulose-6-phosphate to allulose is performed by reacting the allulose-6-phosphate with allulose-6-phosphate phosphatase, a microorganism expressing said allulose-6-phosphate phosphatase, or a culture of the microorganism comprising said allulose-6-phosphate phosphatase.

3. The method according to claim 1, wherein the method further comprises converting glucose-6-phosphate to fructose-6-phosphate by reacting the glucose-6-phosphate with a glucose-6-phosphate isomerase, a microorganism expressing said glucose-6-phosphate isomerase, or a culture of the microorganism comprising said glucose-6-phosphate isomerase, prior to converting the fructose-6-phosphate to allulose-6-phosphate.

4. The method according to claim 3, wherein the method further comprises converting glucose-1-phosphate to glucose-6-phosphate by reacting the glucose-1-phosphate with a phosphoglucomutase, a microorganism expressing said phosphoglucomutase, or a culture of the microorganism comprising said phosphoglucomutase, prior to converting the glucose-6-phosphate to fructose-6-phosphate.

5. The method according to claim 3, wherein the method further comprises converting glucose to glucose-6-phosphate by reacting the glucose with phosphate and a glucokinase, a microorganism expressing said glucokinase, or a culture of the microorganism comprising said glucokinase, prior to converting the glucose-6-phosphate to fructose-6-phosphate.

6. The method according to claim 4, wherein the method further comprises converting starch, maltodextrin, sucrose, or a combination thereof to glucose-1-phosphate by reacting the starch, maltodextrin, sucrose, or combination thereof with phosphate and an α-glucanophosphorylase, starch phosphorylase, maltodextrin phosphorylase, or sucrose phosphorylase; a microorganism expressing said α-glucanophosphorylase, starch phosphorylase, maltodextrin phosphorylase, or sucrose phosphorylase; or a culture of said microorganism comprising said α-glucanophosphorylase, starch phosphorylase, maltodextrin phosphorylase, or sucrose phosphorylase, prior to converting the glucose-1-phosphate to glucose-6-phosphate.

7. The method according to claim 5, wherein the method further comprises converting starch, maltodextrin, sucrose, or a combination thereof to glucose by reacting the starch, maltodextrin, sucrose, or combination thereof with an α-amylase, pullulanase, glucoamylase, sucrase, or isoamylase; a microorganism expressing said α-amylase, pullulanase, glucoamylase, sucrase, or isoamylase; or a culture of said microorganism comprising said α-amylase, pullulanase, glucoamylase, sucrase, or isoamylase, prior to converting the glucose to glucose-6-phosphate.

8. The method according to claim 1, wherein the converting fructose-6-phosphate to allulose-6-phosphate is carried out at a pH of 5.0 to 10.0, a temperature of 50° C. to 90° C., and/or for 1 minute to 24 hours.

9. A method for producing allulose, comprising:
reacting starch, maltodextrin, sucrose, or a combination thereof, and phosphate with:
(a) allulose-6-phosphate phosphatase;
fructose-6-phosphate-3-epimerase consisting of the amino acid sequence of SEQ ID NO: 1;
glucose-6-phosphate isomerase;
phosphoglucomutase or glucokinase; and
α-glucanophosphorylase, starch phosphorylase, maltodextrin phosphorylase, sucrose phosphorylase, α-amylase, pullulanase, isoamylase, glucoamylase, or sucrase;
(b) a microorganism expressing the enzymes of (a), or
(c) a culture of the microorganism of (b) comprising the enzymes of (a),
thereby producing allulose.

10. A method for producing allulose-6-phosphate, comprising: converting fructose-6-phosphate to allulose-6-phosphate by reacting said fructose-6-phosphate with a fructose-6-phosphate-3-epimerase consisting of the amino acid sequence of SEQ ID NO: 1, a microorganism expressing said fructose-6-phosphate-3-epimerase, or a culture of said microorganism comprising said fructose-6-phosphate-3-epimerase.

* * * * *